United States Patent
Zhao

(10) Patent No.: US 9,322,063 B2
(45) Date of Patent: Apr. 26, 2016

(54) EFFICIENT BIOMOLECULE RECYCLING METHOD AND SYSTEM

(75) Inventor: Chanfeng Zhao, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 2530 days.

(21) Appl. No.: 12/020,297

(22) Filed: Jan. 25, 2008

(65) Prior Publication Data

US 2008/0262172 A1 Oct. 23, 2008

Related U.S. Application Data

(60) Provisional application No. 60/897,786, filed on Jan. 26, 2007.

(51) Int. Cl.
*C12Q 1/68* (2006.01)
*C08F 2/00* (2006.01)
*C08G 85/00* (2006.01)

(52) U.S. Cl.
CPC .................................. *C12Q 1/6874* (2013.01)

(58) Field of Classification Search
None
See application file for complete search history.

(56) References Cited

U.S. PATENT DOCUMENTS 6,649,348 B2 * 11/2003 Bass et al. .................... 435/6.19

OTHER PUBLICATIONS

Southern et al. Molecular interactions on microarray. Jan. 1999. Nature Genetics Supplement. vol. 21, pp. 5-9.*

* cited by examiner

*Primary Examiner* — Catherine S Hibbert
*Assistant Examiner* — Channing S Mahatan
(74) *Attorney, Agent, or Firm* — Fletcher Yoder

(57) ABSTRACT

A technique is disclosed for recapturing and recycling biomolecule reagents. The technique may be applied in a range of settings, including biopolymer synthesis, sequencing, and so forth. Biomolecule reagents such as nucleotides and oligonucleotides used to process nucleic acids, which may be marked with fluorescent tags, carry blocking agents, and so forth, are introduced to samples in a sample container. After the desired reaction occurs with some of the biomolecule reagents, such as some of the nucleotides or oligonucleotides, the effluent stream is processed to recapture unreacted biomolecule reagents. These may be separated from other reaction components, and recycled into the same or a different sample container. The recaptured biomolecule reagents may be mixed with additional biomolecule reagents prior to reintroduction to the same or different samples.

22 Claims, 4 Drawing Sheets

EFFICIENT BIOMOLECULE RECYCLING METHOD AND SYSTEM

CROSS REFERENCE TO RELATED APPLICATIONS

This application is a Non-Provisional of U.S. Provisional Patent Application No. 60/897,786, entitled "Efficient Biomolecule Recycling Method and System," filed Jan. 26, 2007, which is herein incorporated by reference.

BACKGROUND

The present invention relates generally to the field of synthesizing, analyzing or otherwise processing molecules such as biologically active molecules or polymers. More particularly, the invention relates to a technique for recapturing or recycling biomolecule reagents including nucleotides or nucleic acids in such processes as synthesis, ligation, sequencing, and so forth.

Nucleotides and nucleic acids are processed for many purposes. Nucleic acids may be used, for example, in research, diagnostics and therapeutics. In general, such nucleic acids may serve as probes that specifically bind to unique sequences of DNA or RNA present in biological samples. This use of nucleic acids may provide for diagnosis of the risk of particular disease states based upon the presence or absence of a particular known gene sequence associated with the disease state. Such nucleotides and nucleic acids (for example, in the form of oligonucleotides) are also used for sequencing lengths or fragments of DNA or RNA from individuals so as to determine their genomic makeup.

Nucleic acid synthesis is typically carried out in a cyclic process that assembles a chain of nucleotides. The nucleotides are added one by one through a series of chemical reactions in which a particular molecule is added to a growing nucleic acid molecule, sometimes via catalysis, until the desired chain is complete. The nucleotides to be added to the chain are typically washed over samples and include blocking molecules that prevent addition of more than one nucleotide at a time in each chain. The blocking molecule is then removed, and the next desired nucleotide may be added in the same way.

Other uses of nucleotides and oligonucleotides include genetic sequencing. Improvements are constantly being made to processes for sequencing nucleic acid segments, which may be supported on a substrate in an array or microarray. In typical DNA sequencing applications nucleotides of the common deoxyribonucleotide types (A, T, C and G) or oligonucleotides containing deoxyribonucleotide monomers are washed over a sample that includes a template DNA to be sequenced and a primer hybridized to the template. A nucleotide or oligonucleotide may bind at a complementary site or sequence of the DNA template that is adjacent to the primer such that the primer is elongated by enzymatically catalyzed addition of the nucleotide or oligonucleotide to the primer. The growing primer is detected in each cycle to determine which nucleotide or oligonucleotide has been incorporated at each site, and the nucleotides are then de-blocked and the cycle repeated. Due to fidelity of the enzymes in specifically adding nucleotides or oligonucleotides that are complementary to the template and rejecting those that are not, the sequence of the template can be determined from the sequence of nucleotides or oligonucleotides added to the primer.

In such processes, nucleotides or oligonucleotides having fluorescent dye markers, blocking molecules, and/or other moieties are typically exposed to the samples in a process fluid. The process fluid also typically contains enzymes that catalyze primer modification. The process fluid is allowed to remain in contact with the sample for a desired time to permit primer modification to take place. The process fluid is then removed in a flush operation, and subsequent processing may occur (e.g., imaging, de-blocking, and so forth). Typically, nucleotides or oligonucleotides are provided in excess amounts to favor high reaction yield. Thus, only a portion of the nucleotides exposed to the samples are consumed and the remainder is flushed away unspent. Similarly, useful enzyme is flushed away after the reaction because under typical conditions the enzyme, being a catalyst, is not consumed.

Current manual and automated systems for both synthesis and sequencing using nucleotides, oligonucleotides and enzymes typically discard these biomolecule reagents contained in the process stream once the stream has been adequately exposed to the sample. However, such molecules can be costly, and the cost of replacing these biomolecule reagents at each cycle can become a significant cost for the overall process.

BRIEF DESCRIPTION

The present invention provides improved techniques for processing molecules such as biopolymers that promises to be more efficient and less costly than heretofore known approaches. The techniques allow for the recapture and eventual recycling of biomolecule reagents used in process fluids. The molecules may include attached fluorescent dyes, blocking moieties, or other moieties that facilitate process chemistry, or may be free of such moieties. The techniques may employ separating one or more of the recaptured biomolecule reagents from one or more other reaction component prior to recycling in the process. Moreover, the technique may be used in a wide range of processes, including synthesis, ligation, sequencing, and so forth. In certain presently contemplated embodiments, the recaptured biomolecule reagents may be mixed with additional biomolecule reagents before being reintroduced into the process. These recycled molecules may then be introduced to the same or a different sample, depending upon the design of the process and the flow of samples through the process.

The present invention provides a method for processing a biopolymer sample. The method can include a step of introducing a process fluid containing biomolecule reagents to a sample container in which a portion of the biomolecule reagents modify a biopolymer sample in the container; processing an effluent stream of the process fluid flowing from the sample container to recapture biomolecule reagents in the effluent stream that are present after the biopolymer sample is modified; and introducing the recaptured biomolecule reagents into the same or a different sample container under conditions for modifying a biopolymer sample with the recaptured biomolecule reagents.

Also provided is a system for processing a biopolymer sample. The system can include a sample container in which a biopolymer sample is disposed; a process fluid introduction subsystem configured to introduce a process fluid containing biomolecule reagents into the sample container in which a portion of the biomolecule reagents modify the biopolymer sample; and an effluent stream processing subsystem configured to process the process fluid flowing from the sample container to recapture biomolecule reagents in the effluent stream that remain after the biopolymer sample is modified, and to recirculate the recaptured biomolecule reagents into the process fluid introduction subsystem for introduction into the same or a different sample container.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
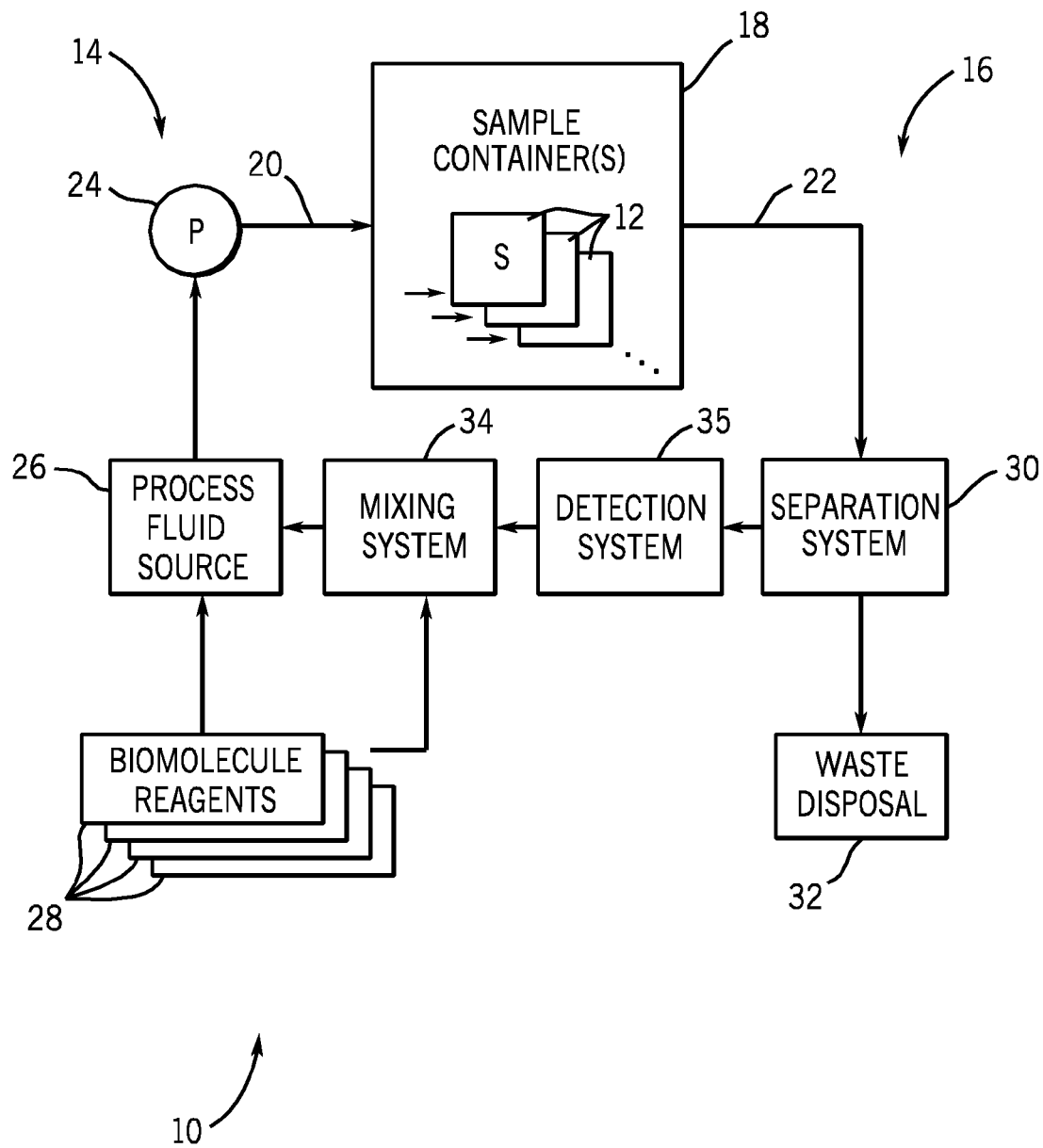
FIG. 1 is a diagrammatical overview of a system for processing biomolecule reagents, such as for synthesis or sequencing making use of the recapture and recycling approach of the invention.

Turning to the drawings, and referring first to FIG. 1, an exemplary processing system 10 is illustrated for processing molecules, such as nucleotides, oligonucleotides or other bioactive reagents. The system may be designed for synthesizing biopolymers, such as DNA chains, or for sequencing biopolymers. Exemplary biopolymers include, but are not limited to nucleic acids such as deoxyribonucleic acid (DNA), ribonucleic acid (RNA), or analogs of DNA or RNA such as those set forth in further detail below. Other exemplary biopolymers include proteins (also referred to as polypeptides), polysaccharides or analogs thereof. Although any of a variety of biopolymers can be used, for the sake of clarity, the systems and methods of the invention will be exemplified with regard to processing nucleic acids.

In general, the illustrated system will act upon samples 12 which may include one reaction site or an array of reaction sites. As used herein, the term "array" refers to a population of different reaction sites on one or more substrates such that different reaction sites can be differentiated from each other according to their relative location. Typically, a single species of biopolymer is attached to each individual reaction site. However, multiple copies of a particular species of biopolymer can be attached to a particular reaction site. The array taken as a whole will typically include a plurality of different biopolymers attached at a plurality of different sites. The reaction sites can be located at different addressable locations on the same substrate. Alternatively, an array can include separate substrates, such as beads, each bearing different reaction sites. Examples of useful arrays are set forth in further detail below where nucleic acid sequencing reactions are described. The sites may include fragments of DNA attached at specific locations in an array, or may be wells in which a target product is to be synthesized. In a presently contemplated embodiment, the processing system 10 may be designed for continuously synthesizing or sequencing molecules, particularly polymeric molecules based upon common nucleotides. For clarity, the system and methods of the invention are exemplified below with regard to particular biopolymer synthesis and sequencing reactions. Those skilled in the art will know or be able to determine other reactions that can be used as well.

In the illustrated embodiment, system 10 includes a process fluid introduction subsystem referred to generally by reference numeral 14, and an effluent stream processing subsystem designated generally by reference numeral 16. The samples themselves will typically be disposed in a sample container 18 through which a process fluid designated generally by line 20 in FIG. 1 is introduced. In general, the process fluid will include various biomolecule reagents that are allowed to react with biopolymers of the samples in each reaction cycle. As discussed below, individual nucleotides of a single type (A, T, C or G) may be contained in the process fluid, such as for synthesizing chains of DNA by cyclic addition of monomers. Alternatively, the process may allow for sequencing by introduction of the four common nucleotide types in the same process fluid such that the nucleotides attach at different sites in each sample. Still further, polymeric biomolecule reagents, such as oligonucleotides used for synthesis by ligation or sequencing by ligation, can be introduced in the process fluid. Other biomolecule reagents that can be introduced include those described below in the context of various sequencing or synthesis techniques. In a typical application, the process fluid introduction subsystem 14 may also deliver a process fluid 20 that includes fluids for flushing the sample, de-blocking molecules, and so forth.

The effluent stream, designated generally by reference numeral 22, can include nucleotides, and oligonucleotides (if used in the process stream) that did not react with the sample during a reaction cycle. In general, the process fluid introduced for such reactions will include many times more nucleotides and/or oligonucleotides than are required for the synthesis or sequencing process. Additionally or alternatively, the effluent stream can include an enzyme, such as a polymerase or ligase, that remains active following the reaction cycle. The effluent stream may be drained from the samples in various manners, but in a presently contemplated embodiment, the stream is created by control of valving (not shown) that allows the flow of fluids from the container or containers 18 after sufficient time has elapsed for the reaction cycle. The process fluid may be forced through the system by one or more pumps, as indicated by reference numeral 24 for a pump in a process fluid introduction subsystem 14. The pump will typically draw process fluids from a source 26 where biomolecule reagents such as nucleotides and enzymes introduced into the system, as indicated by reference numeral 28, are mixed with other fluids and reagents. Other pumps and appropriate conduits, valving, and so forth (not shown) will typically be provided for other fluids and reagents, such as those used for flushing the sample container after a reaction cycle, de-blocking nucleotides and oligonucleotides, and so forth.

As will be appreciated by those skilled in the art, biomolecule reagents 28 added to the process stream during any particular cycle of operation may include only one of the common DNA nucleotides, such as where oligonucleotides of specific sequences are to be synthesized. For sequencing, on the other hand, all four common nucleotides may be included in the process stream introduced to the samples during each cycle of operation. Again, depending upon the nature of the process, these nucleotides may be tagged with fluorescent markers such that they can be easily imaged during each cycle of operation. In other systems, the biomolecule reagents 28 will be replaced by oligonucleotides which will be introduced to the samples, such as for ligation. In such processes, the introduced oligonucleotides will typically be tagged for fluorescent imaging. Other biomolecule reagents 28 that can be added are set forth below in the context of different synthesis and sequencing techniques. Those skilled in the art will know or be able to readily determine various combinations of the reagents based on the concepts exemplified for nucleic acid processing and that which is described below or otherwise known for the different synthesis and sequencing techniques.

The effluent stream processing subsystem 16 may include a separation system 30 that isolates the nucleotides, enzymes and/or other biomolecule reagents from certain other constituents and reagents of the effluent stream. Several different types of separation methods may be envisaged for this purpose, such as filtration; solid-phase extraction; liquid phase extraction; chromatographic techniques such as size exclusion chromatography (SEC), ion exchange chromatography, reverse phase chromatography, normal phase (silica) chromatography, affinity chromatography; electrophoresis or the like. A method appropriate for the particular biomolecule reagent can be used. If desired, the method can be specific for only a subset of the biomolecule reagents to be recycled. For example, the method can separate nucleotides from enzymes or can even separate different species of nucleotides from each other. However, it is also possible to use a method that co-isolates all four species of nucleotides together or co-isolates nucleotides and enzymes.

The separation system 30 can further function to concentrate a biomolecule reagent that is separated from the effluent stream. Concentration can be a byproduct of the particular separation method used. For example, SEC and solid phase extraction typically have the effect of eluting biomolecule reagents in a more concentrated form. If desired, the separation system can include a subsystem that is capable of concentrating a biomolecule reagent of interest prior to recycling or a separate concentration step can be included prior to recycling. Concentration can be carried out by SEC, solid phase extraction, precipitation, and/or removal of solvent by evaporation or other known method.

The separation system 30 may output two separate process streams, one including recaptured enzymes, nucleotides or oligonucleotides, and a second waste stream which is forwarded for waste disposal as indicated by reference numeral 32 in FIG. 1. Such fluids may be disposed of in any conventional manner. The recaptured nucleotides or oligonucleotides may be mixed with additional nucleotides or oligonucleotides as indicated generally by reference numeral 34 in FIG. 1. Depending upon the volume or flow rate desired for the system, and the amount and type of nucleotides or oligonucleotides recaptured by the system, and the percentage balances of recaptured material and additional material may be controlled by the mixing system 34. This material may then be advanced to the process fluid source 26 for reintroduction to the same sample or sample container, or to different samples or different sample containers.

A detection system 35 can be included in the system of FIG. 1 to allow quantitation of enzymes, nucleotides, or oligonucleotides that are to be recycled. The detection system can be placed to detect biomolecule reagents that are separated by the separation system 30 prior to delivery of the reagents to the mixing system 34 (or prior to delivery to the process fluid source 26 in embodiments that do not include the mixing system 34). Detection can be via any technique that is appropriate to quantitate a distinguishing property of a biomolecule reagent of interest. Exemplary properties upon which detection can be based include, but are not limited to, mass, electrical conductivity, energy absorbance, fluorescence, magnetism, luminescence, or the like. For example, nucleotides, oligonucleotides, or enzymes having a fluorescent label can be quantified using a UV/VIS detector or fluorimeter that detects light absorbance or emission in a wavelength that is specific to the label. Other detection techniques that can be used include, for example, mass spectrometry which can be used to perceive a biomolecule reagent based on its mass; surface plasmon resonance which can be used to perceive a biomolecule reagent based on binding or dissociation from a surface; electrical conductance or impedance which can be used to perceive a biomolecule reagent based on changes in its electrical properties or in the electrical properties of its environment; magnetic resonance which can be used to perceive a biomolecule reagent based on presence of magnetic nuclei; or other known analytic spectroscopic or chromatographic techniques.

The detection system 35 can interface with a computer that is capable of processing detected signals to determine the quantity of a particular recaptured biomolecule reagent of interest. The computer can further be programmed to determine an appropriate amount of additional biomolecule reagent to add to the recaptured biomolecule reagent at mixing system 34 in order to provide a desired quantity of biomolecule reagent for the next cycle of the sequencing or synthesis reaction being carried out. In this way recycling can be carried out in a fully automated fashion without intervention of a human user for one or more cycles of a sequencing or synthesis reaction. Alternatively or additionally, the system can be configured to report the quality or quantity of the recaptured biomolecule reagent to a human user.

Figure 2:
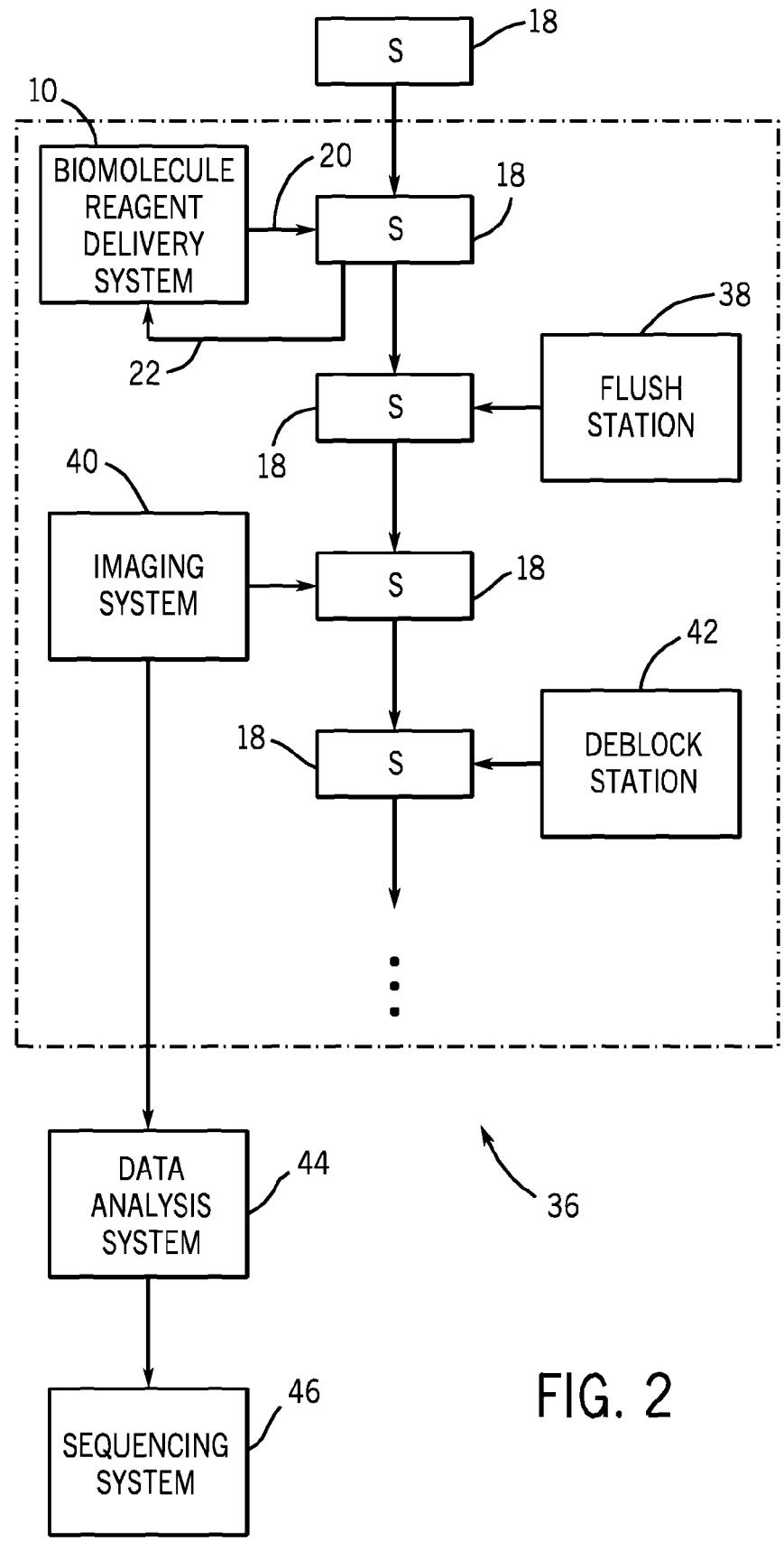
FIG. 2 is a diagrammatical overview of an exemplary multi-station processing system, such as one used for sequencing.

FIG. 2 is a diagrammatical overview of a biopolymer processing system 36 that may employ a biomolecule reagent delivery system 10 of the type discussed with reference to FIG. 1. In general, system 36 may include a plurality of stations through which samples in sample containers 18 progress. The system may be designed for cyclic operation in which reactions are promoted with single nucleotides or with oligonucleotides, followed by flushing, imaging and de-blocking in preparation for a subsequent cycle. In a practical system, the samples 18 may be circulated through a closed loop path for sequencing, synthesis or ligation.

In the illustrated embodiment, the nucleotide delivery system 10 provides process stream 20 to a sample container 18. As discussed with reference to FIG. 1, then, the effluent stream 22 from the container is recaptured and recirculated in the nucleotide delivery system, for recapture of enzymes, nucleotides and oligonucleotides (where used) from the effluent stream. These are recycled, such as with additional enzymes, nucleotides or oligonucleotides being added, as discussed above with reference to FIG. 1. In the illustrated embodiment, then, the sample container may be flushed at a flush station 38 to remove additional reagents and to clarify the sample for imaging. The sample is then moved to an imaging system 40 where image data may be generated that can be analyzed for determination of the sequence of a progressively building oligonucleotide chain, such as based upon a known template as described below. In a presently contemplated embodiment, for example, imaging system 40 may employ confocal line scanning to produce progressive pixilated image data that can be analyzed to locate individual sites in an array and to determine the type of nucleotide that was most recently attached or bound to each site. Following imaging station 40, then, the samples may progress to a de-blocking station 42 in which a blocking molecule or protecting group is cleaved from the last added nucleotide, along with the marking dye.

In a typical sequencing system, then, image data from the imaging system 40 will be stored and forwarded to a data analysis system as indicated generally at reference numeral 44. The analysis system will typically include a general purpose or application-specific programmed computer providing for user interface and automated or semi-automated analysis of the image data to determine which of the four common DNA nucleotides was last added at each of the sites in an array of each sample. As will be appreciated by those skilled in the art, such analysis is typically performed based upon the color of unique tagging dyes for each of the four common DNA nucleotides. However, tags having other distinguishing properties, whether detectable by imaging or any other useful method, can be used if desired including, for example, tags having those properties set forth above in regard to the detection system of FIG. 1. This image data is further analyzed by a sequencing system 46 which may derive sequence data from the image data, and piece together sequence data for a multitude of oligonucleotides or DNA fragments to provide more comprehensive genomic mapping of a particular individual or population.

Figure 3:
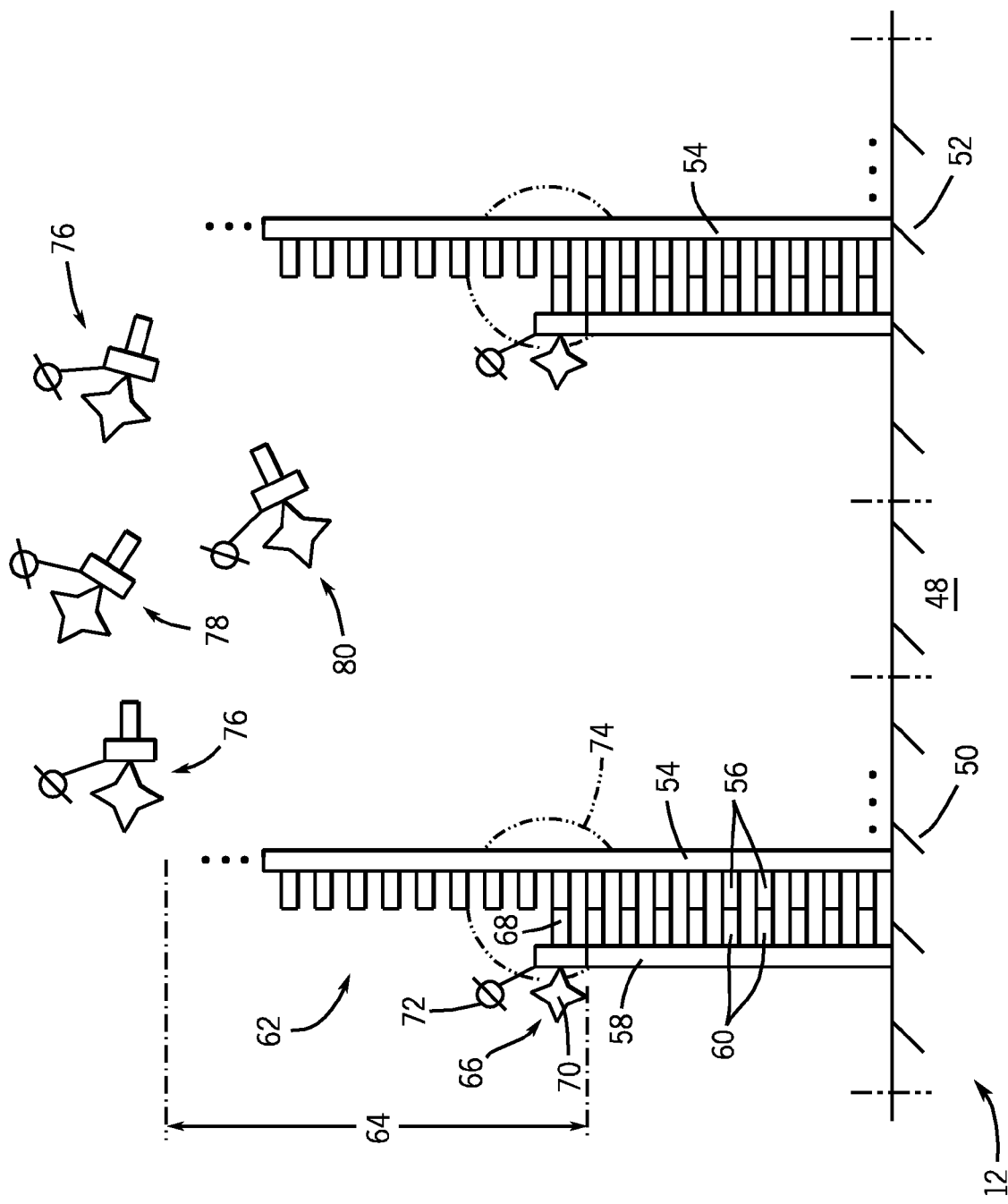
FIG. 3 is a diagrammatical summary of how nucleotides may be introduced to samples for sequencing the samples in an array through systems such as those shown in FIGS. 1 and 2.

FIG. 3 illustrates a typical reaction cycle in a sequencing by synthesis technique for oligonucleotides that may benefit from the nucleotide recapture and recycling technique of the present invention. In general, the synthesis operation summarized in FIG. 3 may be performed on a sample 12 comprising a support 48 on which a multitude of sites 50 and 52 are formed. In the preparation of each sample 12, many such sites may be formed, each with unique fragments of genetic material as indicated generally by reference numeral 54. These fragments may constitute templates of DNA or RNA to be sequenced. The fragments can be isolated from a biological source using methods known in the art. In embodiments utilizing amplification methods, the fragments can be amplicons of a DNA or RNA isolated from a biological source. Each template comprises a number of mers or bases 56 which will uniquely bind to a complimentary nucleotide (or analog thereof) during the synthesis process. The sequencing process begins with binding of an anchor primer 58 to each of the templates. This anchor primer includes complimentary bases 60 that bind with those of a corresponding sequence of the template. The remaining portion of the template, designated generally by reference numeral 62, constitutes that portion to be sequenced. The length 64 of this portion may vary, with presently contemplated embodiments extending from 25 to 40 bases or more.

As sequencing progresses, the introduced processed stream will include all four common DNA nucleotides, one of which will add to the primer at a position that is opposite the next available base in the template, as indicated by reference numeral 66. The added nucleotide will include a base 68 that is complementary to the template as well as a fluorescent tag 70 and a blocking molecule 72. As will be noted by those skilled in the art, as used herein, the term "nucleotides" in the illustrated processes will typically include units from which DNA molecules are constructed. Although any nucleotides or oligonucleotides may be recaptured and recycled in accordance with the present technique, in many practical applications, these will include deoxynucleotide-triphosphates (dNTP), each carrying a single nitrogenous base (adenine, guanine, cytosine or thymine). The complimentary nucleotide is added to the primer due to the activity of a polymerase, as indicated generally by reference numeral 74. Other nucleotides than the specific one binding to the template will also be present in the process fluid, as indicated generally by reference numerals 76, 78 and 80 in FIG. 3. Nucleotides not binding to the templates will subsequently be washed from the sample in a flushing operation, exiting in the effluent stream to be recaptured and recycled as described above.

Figure 4:
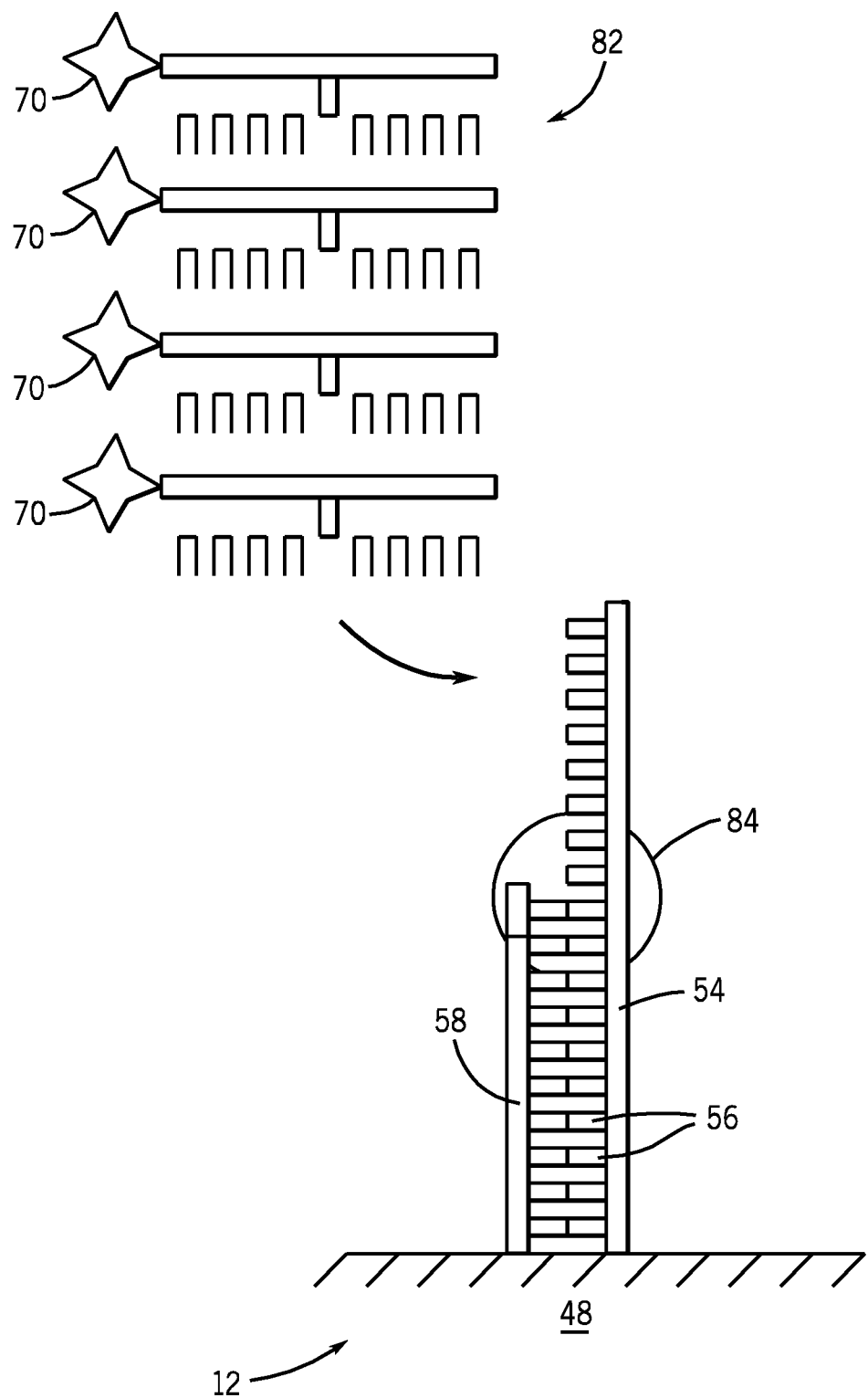
FIG. 4 is a diagrammatical representation of the use of oligonucleotide in sequencing by ligation.

FIG. 4 is a diagrammatical representation of a sequencing by ligation reaction. As in the case of FIG. 3, the sample 12 may include sites formed on a support 48. Each site may include a unique fragment of genetic material or a template 54 to be sequenced. The ligation process also begins with binding of an anchor primer 58 to the template. However, in the ligation reaction, query probes 82, each carrying a unique fluorescent tag 70 are introduced to the sample in a process stream. The primers may bind to a query position on the template and be added to the primer in the presence of ligase as indicated generally by reference numeral 84. In general, each of the query probes will include a single dNTP base which attaches to a corresponding location on the template. As in the previous example, the oligonucleotides comprising the query primers are then washed from the sample in a flushing operation, recaptured and recycled as described above. The sequencing by ligation reaction can include a step of removing part of the sequence of the added probe using a restriction endonuclease as set forth in further detail below. The restriction endonuclease can also be recycled using methods set forth herein. There is a variety of nucleic acid sequencing methods that can be used in accordance with the methods set forth herein, most of which involve cycle sequencing consisting of repeated rounds of sequencing biochemistry interspersed by imaging. Several formats of cycle sequencing have been described in the literature, and include sequencing-by-synthesis (SBS), sequencing-by-ligation (SBL), and sequencing-by-hybridization (SBH). One of the most useful forms of cycle sequencing is SBS, an embodiment of which has been described above in regard to FIG. 3. In SBS the sequence of a target nucleic acid is read by repeated rounds of polymerase-based nucleotide insertion and fluorescent/chemiluminescent readout. SBS has two formats: (1) stepwise nucleotide addition (SNA) employing cycles of dNTP incorporation and imaging, and (2) cyclic reversible termination (CRT) employing cycles of incorporation of reversible terminators, imaging, and deprotection.

The SNA approach to cycle sequencing has been described by at least three different groups. In one commercial implementation from 454 Lifesciences, (Branford, Conn.) and Roche Diagnostics (Basel, Switzerland), cyclic pyrosequencing from assembled clonal beads has been used to sequence entire microbial genomes. Other examples of SNA include those that use cyclic addition of cleavable fluorescently-labeled dNTPs to sequence polony clones. After each base addition and imaging step, fluorescent labels are cleaved by disulfide reduction. In a third approach, single target molecules are immobilized onto a glass microscope slide at a sparse density and cycle sequencing is performed by basewise addition of Bodipy-labeled dNTPs. After imaging, the fluorescence was destroyed by photobleaching.

In CRT, cycle sequencing is accomplished by stepwise addition of reversible terminator nucleotides containing a cleavable or photobleachable dye label. This approach is being commercialized by Solexa. The availability of fluorescently-labeled terminators in which both the termination can be reversed and the fluorescent label cleaved is important to facilitating efficient CRT. Polymerases can also be co-engineered to efficiently incorporate and extend from these modified nucleotides. In particular embodiments, reversible terminators/cleavable fluors can include fluor linked to the ribose moiety via a 3' ester linkage. Other approaches have separated the terminator chemistry from the cleavage of the fluorescence label. For example, reversible terminators are known that include a small 3' allyl group that blocks extension until it is deblocked by a short treatment with a palladium catalyst. The fluorophore can be attached to the base via a photocleavable linker that can be cleaved by exposure to long wavelength UV light. Thus, both disulfide reduction or photocleavage can be used as a cleavable linker.

Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination.

The biomolecule reagents used in the above-described sequencing methods can be recycled using a method or system of the invention. Based on the principles and examples set forth herein, those skilled in the art will be able to readily apply the methods and systems of the invention to different sequencing techniques.

Oligonucleotide synthesis is a cyclical process that assembles a chain of nucleotides. Nucleotides are added one by one through a cycle of chemical reactions, in which a particular molecule (e.g., a nucleotide) is added to a growing DNA molecule (e.g., a growing DNA chain), sometimes via catalysis, until the desired chain is complete. Generally, each cycle of chemical reactions includes the steps of detritylation, coupling, capping and oxidation. During the detritylation or "deprotection" step, a dimethoxytrityl (DMT) group is removed from the last nucleotide of the growing DNA chain to allow the addition of the next nucleotide. The amount of DMT released from each cycle is monitored to determine coupling efficiency. The release of DMT is apparent because a bright orange color is emitted as DMT is released. In accordance with the systems and methods set forth herein, unused nucleotides that are present after individual synthetic cycles can be recycled for use in a subsequent cycle.

Any of a variety of nucleic acids can be synthesized or sequenced using the invention including, for example, those having a native structure or those having an analog structure. A nucleic acid with a native structure generally has a backbone containing phosphodiester bonds and can be, for example, deoxyribonucleic acid or ribonucleic acid. An analog structure can have an alternate backbone including, without limitation, phosphoramide, phosphorothioate, phosphorodithioate, O-methylphosphoroamidite linkages, or peptide nucleic acid backbones and linkages. Other analog structures include those with positive backbones, non-ionic backbones, and non-ribose backbones. Analog structures containing one or more carbocyclic sugars are also useful.

A nucleic acid useful in the invention can contain a non-natural sugar moiety in the backbone. Exemplary sugar modifications include, but are not limited to, 2' modifications such as addition of halogen, alkyl, substituted alkyl, SH, $SCH_3$, OCN, Cl, Br, CN, $CF_3$, $OCF_3$, $SO_2CH_3$, $OSO_2$, $SO_3$, $CH_3$, $ONO_2$, $NO_2$, $N_3$, $NH_2$, substituted silyl, and the like. Similar modifications can also be made at other positions on the sugar, particularly the 3' position of the sugar on the 3' terminal nucleotide or in 2'-5' linked oligonucleotides and the 5' position of 5' terminal nucleotide. Such modifications provide useful moieties for blocking further extension of nucleic acids that have incorporated the analogs. Such moieties are referred to as "blocking groups." Nucleic acids, nucleoside analogs or nucleotide analogs having sugar modifications can be further modified to include a reversible blocking group, peptide linked label or both.

A nucleic acid used in the invention can also include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. Exemplary non-native bases that can be included in a nucleic acid, whether having a native backbone or analog structure, include, without limitation, inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702. A non-native base used in a nucleic acid of the invention can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which basepairs with cytosine, adenine or uracil.

Nucleotide precursors for the above-described nucleic acids and analogs are known in the art and can be used in the systems or methods set forth herein. Furthermore, primers or other oligonucleotides used for sequencing or synthesizing nucleic acids or nucleic acids can include one or more of the above-described structures or biological activities.

Although the methods and systems of the invention have been exemplified above with regard to nucleic acids for clarity, it will be understood that any of a variety of biopolymers can be synthesized, analyzed or otherwise processed using a system or method disclosed herein. Embodiments that are directed to peptide synthesis can be carried out to recapture and recycled biomolecule reagents used in the method set forth below.

The process of peptide synthesis on solid supports generally involves building a peptide from the carboxyl-terminal end. The peptide is attached to a solid support via its carboxy-terminal amino acid and further includes a protecting group on the amino-terminal α-amino group. The protecting group is then cleaved off of the peptide to form a deprotected peptide. Next, a monomeric amino acid, also containing an α-amino protecting group, is contacted with the de-protected peptide under conditions for formation of a peptide bond between the α-amino group of the deprotected peptide and the α-carboxy group the monomeric amino acid. The monomeric amino acid can be provided in an activated form or an activating reagent can be added to the amino acid and growing peptide. Washes can be carried out between steps to remove reagents. The cycle of deprotecting the prior amino acid and coupling the additional amino acid can be repeated until a peptide of the desired length is synthesized. Any reactive side chains of the amino acids are typically protected by chemical groups that can withstand the coupling and α-amino deprotection procedure. These side chain protecting groups, however, can be removed at the end of the synthesis.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for processing a biopolymer sample comprising:
   a sample container in which a biopolymer sample is disposed;
   a process fluid introduction subsystem configured to introduce a process fluid containing biomolecule reagents into the sample container in which a portion of the biomolecule reagents modify the biopolymer sample;
   an effluent stream processing subsystem configured to process the process fluid flowing from the sample container to recapture biomolecule reagents in the effluent stream that remain after the biopolymer sample is modified; and
   a mixing subsystem configured to mix the recaptured biomolecule reagents with biomolecule reagents from the process fluid introduction subsystem to produce mixed biomolecule reagents, wherein the system is further configured to recirculate the mixed biomolecule reagents into the sample container.

2. The system of claim 1, comprising a separation subsystem configured to separate the biomolecule reagents from other components of the effluent stream prior to the recirculation of the mixed biomolecule reagents into the sample container.

3. The system of claim 1, wherein the system is configured to determine the sequence of the biopolymer sample.

4. The system of claim 3, wherein the biopolymer sample comprises a nucleic acid.

5. The system of claim 4, further comprising a process fluid that comprises nucleotides or oligonucleotides.

6. The system of claim 4, further comprising a process fluid that comprises a polymerase or ligase.

7. The system of claim 1, wherein the system is configured to synthesize a biopolymer.

8. The system of claim 7, wherein the biopolymer comprises a nucleic acid.

9. The system of claim 1, wherein the system is configured to quantify a biomolecule reagent in the effluent stream.

10. The system of claim 1, wherein the system is configured to retain the biopolymer sample in the sample container by attachment to a solid phase substrate.

11. The system of claim 1, wherein the system is configured to process a plurality of different biopolymer samples, whereby a plurality of different biopolymer samples are disposed in the sample container, and whereby the process fluid introduction subsystem is configured to introduce a process fluid containing biomolecule reagents into the sample container in which a portion of the biomolecule reagents modify the plurality of different biopolymer samples.

12. The system of claim 11, wherein the plurality of different biopolymer samples comprises at least 1,000 different biopolymers attached to individual sites of an array.

13. The system of claim 1, comprising a reagent concentration subsystem configured to concentrate the recaptured biomolecule reagents prior to the recirculation of the mixed biomolecule reagents into the sample container.

14. A system for processing a biopolymer sample, comprising:
   a plurality of sample containers in which a biopolymer sample is disposed;
   a process fluid introduction subsystem configured to introduce a process fluid containing biomolecule reagents into the plurality of sample containers in which a portion of the biomolecule reagents modify the biopolymer sample;
   an effluent stream processing subsystem configured to process the process fluid flowing from the plurality of sample containers to recapture biomolecule reagents in the effluent stream that remain after the biopolymer sample is modified; and
   a mixing subsystem configured to mix the recaptured biomolecule reagents with biomolecule reagents from the process fluid introduction subsystem to produce mixed biomolecule reagents, wherein the system is further configured to recirculate the mixed biomolecule reagents into a sample container of the plurality of sample containers.

15. The system of claim 1, wherein the mixing subsystem controls percentage balances between the recaptured biomolecule reagents and the biomolecule reagents from the process fluid introduction subsystem.

16. The system of claim 15, wherein the percentage balances are based at least in part on a desired volume or flow rate through the sample container.

17. The system of claim 15, wherein the percentage balances are based at least in part on properties of the recaptured biomolecule reagents.

18. The system of claim 17, comprising a detection system disposed between the effluent stream processing subsystem and the mixing subsystem, wherein the detection system is configured to determine the properties of the recaptured biomolecule reagents.

19. The system of claim 14, wherein the mixing subsystem controls percentage balances between the recaptured biomolecule reagents and the biomolecule reagents from the process fluid introduction subsystem.

20. The system of claim 19, wherein the percentage balances are based at least in part on a desired volume or flow rate through the plurality of sample containers.

21. The system of claim 19, wherein the percentage balances are based at least in part on properties of the recaptured biomolecule reagents.

22. The system of claim 21, comprising a detection system disposed between the effluent stream processing subsystem and the mixing subsystem, wherein the detection system is configured to determine the properties of the recaptured biomolecule reagents.

* * * * *